United States Patent [19]

Columbus

[11] 4,271,119
[45] Jun. 2, 1981

[54] CAPILLARY TRANSPORT DEVICE HAVING CONNECTED TRANSPORT ZONES

[75] Inventor: Richard L. Columbus, Rochester, N.Y.

[73] Assignee: Eastman Kodak Company, Rochester, N.Y.

[21] Appl. No.: 142,942

[22] Filed: Apr. 23, 1980

Related U.S. Application Data

[63] Continuation-in-part of Ser. No. 59,816, Jul. 23, 1979, abandoned, which is a continuation-in-part of Ser. No. 954,689, Oct. 25, 1978.

[51] Int. Cl.³ .................... G01N 1/00; G01N 27/46; G01N 31/22
[52] U.S. Cl. .................... 422/50; 204/195 R; 204/195 M; 204/195 B; 422/58; 422/100
[58] Field of Search .................... 422/50, 55–58, 422/68, 99, 100; 204/195 R, 195 M, 195 B; 356/244; 435/4, 310; 23/230 R, 230 B

[56] References Cited

U.S. PATENT DOCUMENTS

| | | | |
|---|---|---|---|
| 3,690,836 | 9/1972 | Buissiere et al. | 422/56 |
| 3,715,192 | 2/1973 | Wenz et al. | 422/56 |
| 3,764,018 | 10/1973 | Shaw et al. | 210/500 |
| 3,783,696 | 1/1974 | Coleman | 422/100 X |
| 4,053,381 | 10/1977 | Hamblen et al. | 204/195 M |
| 4,184,936 | 1/1980 | Paul et al. | 204/195 R |

*Primary Examiner*—Arnold Turk
*Attorney, Agent, or Firm*—Dana M. Schmidt

[57] ABSTRACT

A device is disclosed comprising first and second capillary liquid transport zones provided by first and second pairs of opposing surfaces, the opposing surfaces of the second zone both extending from the same one of the paired surfaces of the first zone. The inlet to the second zone is a diverting aperture that is formed in such same surface and configured (i) to insure complete wetting of the second pair of surfaces by the liquid and (ii) to provide a cross-sectional flow-through area greater than about 0.2 mm².

10 Claims, 18 Drawing Figures

COMPARATIVE EXAMPLE

CAPILLARY TRANSPORT DEVICE HAVING CONNECTED TRANSPORT ZONES

RELATED APPLICATIONS

This application is a continuation-in-part application of U.S. Application Ser. No. 059,816, filed on July 23, 1979, entitled "Electrode-Containing Device with Capillary Transport Between Electrodes", now abandoned, which in turn is a continuation-in-part of U.S. Ser. No. 954,689, filed on Oct. 25, 1978, entitled "Liquid Transport Device and Method".

FIELD OF THE INVENTION

This invention is directed to a device and a method for transporting liquid by capillary attraction into different zones.

BACKGROUND OF THE INVENTION

Capillary transport devices have been constructed with two surfaces spaced to cause flow of introduced liquid by capillary action, thus creating between such surfaces a zone of intended liquid transport. When the two surfaces are two opposed sheets sealed around their edges, liquid is introduced through an access aperture formed in one of the sheets, and trapped air vented, e.g., by a separate aperture. Such capillary transport devices have been used for analyzing liquids; one such device being shown in U.S. Pat. No. 3,690,836 wherein one of the opposing surfaces is an absorbent reagent-containing layer. The transported liquid reacts with the imbibed reagents to produce a visible color indicative of the analyte.

The above-described devices are generally limited to capillary flow between the opposing surfaces. Such flow distributes the liquid to, e.g., two absorbent test areas that define in part the opposing surfaces, as shown for example, in U.S. Pat. No. 3,715,192, issued Feb. 6. 1973. However, the number of different test areas that are possible is limited by the number that can fit within the total surface areas of the zone that are to be wetted by the liquid.

In my aforesaid related application Ser. No. 954,689, the liquid transport device described therein is capable of diverting flow to individual test areas or zones. Such zones, through separate, are provided by a pair of opposing surfaces that are extensions of the pair of surfaces providing the first transport zone. That is, each separate test zone branch extends from an opening formed by both opposing walls or surfaces providing the first zone.

Although such branching features are highly useful, there is a limit to the number of branches that can extend from openings formed by both the opposing walls. If additional zones could be extended from only one of the surfaces of the first zone, then additional tests could be conducted in such additional zones.

Prior to this invention liquid transport devices did provide additional capillary zones created by relatively small diverting apertures having a cross-sectional flow-through area of 0.2 mm$^2$ or less. "Cross-sectional flow-through area" is used herein to mean the area measured transverse to liquid flow through that area. This area limitation was necessary, because with preferred hydrostatic heads and prior art aperture configurations liquid would not divert into larger apertures. Examples of such small diverting apertures, generally circular in shape, can be found in conventional devices.

The problem, however, is that the prior art transport zones fed by such small area apertures created sharply-curved menisci that would not wet a solid test element disposed at the end of the zone. Thus, one problem has been to devise a diverting aperture that will provide capillary flow in a zone of sufficient cross-sectional area to properly wet a solid test element at the end of the zone.

Still another drawback of apertures of 0.2 mm$^2$ cross-sectional flow-through area or less is that test elements that are area dependent, such as ion-selective elements, tend not to develop a useful signal for such small cross-sectional flow-through areas.

OTHER APPLICATIONS

My U.S. Application Ser. No. 118,840, filed on Feb. 6, 1980, entitled "Multi-Analyte Test Device" is directed to a liquid capillary transport zone that transports a drop of liquid to a multiple number of radiometric test sites.

SUMMARY OF THE INVENTION

This invention is based on the discovery that a diverting aperture can be constructed with a flow-through area larger than was possible with prior devices. It is such larger apertures that permit the radius of curvature of the meniscus of the second zone to be reduced to a value useful for wetting solid test elements as described above. Additionally, larger volumes of liquid are provided for testing.

In accordance with one aspect of the invention, there is provided an improved liquid transport device of the kind wherein a first zone of intended capillary liquid transport is formed by a first pair of opposing surfaces spaced apart a distance effective to induce capillary flow of introduced liquid. Liquid access means are provided so that introduced liquid flows in the first zone from the access means by capillary attraction. This device is improved by the addition of at least a second pair of opposing surfaces spaced apart a distance effective to induce capillary flow of introduced liquid within the second zone and to provide a second zone of intended capillary liquid transport. The second pair of surfaces extends from only one surface of the first pair of surfaces, and diverting means are included in the one surface for directing a portion of the capillary liquid flow away from the first zone into the second zone while the remainder of the liquid continues flowing in the first zone. The diverting means is configured to insure complete wetting of the second pair of surfaces by the liquid moving therepast and to provide a cross-sectional flow-through area greater than about 0.2 mm$^2$. As used herein, "greater than about 0.2 mm$^2$" means, by an amount that is statistically significant, e.g., is greater than variations produced by experimental error in measuring the area.

Thus, one advantage of the present invention is that subsequent processing of the liquid, such as by analytical tests, need not be limited to a single zone created by the first pair of opposing surfaces, but can be carried out in a multiplicity of zones, all of which are filled by depositing a quantity of liquid into a single access means.

Another advantage of the invention is that the multiple zones can be automatically supplied by liquid all without the necessity for active driving elements such as pumps.

Other features and advantages will become apparent upon reference to the following Description of the Preferred Embodiments when read in light of the attached drawings.

DESCRIPTION OF THE PREFERRED EMBODIMENTS

The device of the invention is capable of providing from a single first capillary zone, an increased number of processing or test loci for liquid supplied thereto. This is achieved by the creation of additional capillary transport zones each of which extends from either one of the surfaces of the first zone. This invention has been rendered possible by the discovery of a diverting means that effectively draws off at one of the surfaces defining the first zone a new, useful capillary stream while allowing the first capillary stream to continue to flow in the first transport zone. A preferred form of such diverting means is a specially shaped aperture, as hereinafter described.

The embodiments which follow refer to whole blood or blood serum as the preferred transport liquid. In addition, other liquids can be transported, including other biological liquids and industrial liquids, such as photographic developer solutions.

Figure 1:
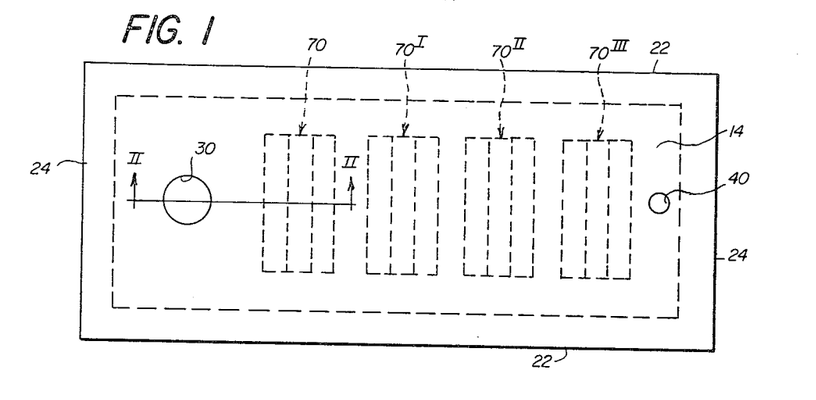
FIG. 1 is a plan view of a device constructed in accordance with the invention.
Figure 2:
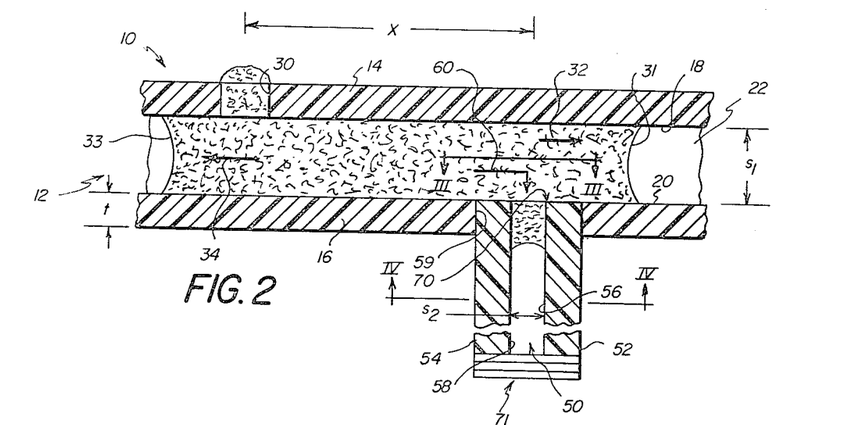
FIG. 2 is a fragmentary section view taken generally along the line II—II of FIG. 1.

A liquid transport device 10 of the invention comprises, FIGS. 1-2, a first transport zone 12 comprising two members 14 and 16 having opposing interior surfaces 18 and 20, FIG. 2, spaced apart a distance $s_1$, that is effective to induce liquid to flow between the surfaces by capillary action alone. Sidewalls 22 and 24, FIG. 1, are used to mount members 14 and 16 in this spaced-apart relation, with or without bridging studs (not shown) within the zone. Walls 22 and 24 are secured to members 14 and 16 by any conventional means, including water-insoluble adhesives or ultrasonic bonding.

To permit introduction of liquid into zone 12, a liquid access aperture 30 is provided in one of members 14 and 16, preferably 14, thereby defining a locus of liquid introduction. A quantity of liquid is be deposited at aperture 30, either in drop form, or as a quantity that is injected into the aperture. Because of the capillary spacing $s_1$, the injecting pressure need not be so large as to fill zone 12 by the pressure alone.

The size of aperture 30 is selected to insure that the volume of liquid introduced will contact both surfaces 18 and 20, to initiate transport of liquid menisci 31 and 33 through zone 12 in the direction of arrows 32 and 34, respectively, FIG. 2. If a 10 μl sized drop is necessary for proper liquid flow, aperture 30 can be, e.g., about 1.0 mm to about 5.0 mm in diameter. Alternatively, aperture 30 can have cornered sidewalls, not shown, so as to have the shape of, e.g., a hexagon instead of a circle, to insure more positive movement of the liquid into the aperture.

As the liquid advances within zone 12, air is entrapped. To vent the air, at least one vent aperture 40 is provided, FIG. 1, preferably at the end of zone 12 that is opposite to the locus of liquid introduction defined by aperture 30. Alternatively, aperture 40 can be disposed in one or more of the sidewalls 22 and 24, or in member 16. The size of vent aperture 40 is not critical. Generally, it is smaller than that of aperture 30.

Yet another variation is to provide grooves, not shown, in surfaces 18 and 20 to control the shape of the menisci 31 and 33 as they advance. Such grooves preferably are mutually parallel within a given surface and the grooves of opposing surface portions are disposed at a finite angle.

It will be readily appreciated that a number of areas are available on surfaces 18 and 20 to process or test the liquid that is transported through zone 12. For example, a portion of zone 12 downstream from meniscus 31 is reserved for microscopic viewing of the liquid, as are a plurality of other portions throughout the zone.

Figure 4:
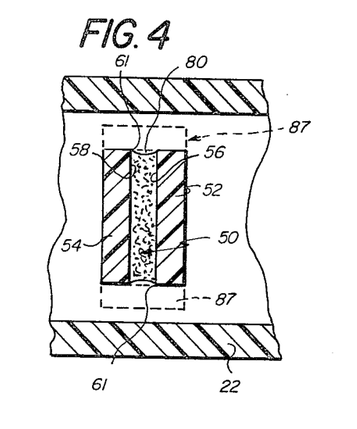
FIG. 4 is a fragmentary section view taken generally along the line IV—IV of FIG. 2.

In accordance with one aspect of the invention, a second liquid capillary transport zone 50 is provided, FIGS. 2 and 4, which diverges from first zone 12 so as to create additional areas for testing or processing of the liquid. Zone 50 is defined by a second pair of members 52 and 54 having opposed interior surfaces 56 and 58, respectively, spaced apart a capillary distance $s_2$, FIG. 2. Members 52 and 54 comprise generally planar sheets mounted in an aperture 59 which extends only a portion of the distance between sidewalls 22. Preferably there is a distance z from the aperture edge 69 to each sidewall 22, measuring at least about 2.0 mm. Bridging studs, not shown, can be disposed between members 52 and 54 within the second zone 50 to maintain spacing $s_2$. As shown, $s_2$ equals the aperture width w, but as described hereinafter, spacing $s_2$ can be increased as zone 50 extends away from zone 12. To vent trapped air from zone 50, part or all of edges 61, FIG. 4, of surfaces 56 and 58, are left open to the atmosphere. Surfaces 56 and 58 can be either grooves or smooth, as described for surfaces 18 and 20.

To divert a portion of the liquid flowing through zone 12 in the direction of arrow 60 and into capillary flow within zone 50, surfaces 56 and 58 of zone 50 form a predetermined aperture 70 in surface 20 at a locus downstream from aperture 30. Aperture 70 is configured to have two characteristics. First, it has a total cross-sectional area, measured transverse to liquid flow therethrough, that is greater than 0.2 mm$^2$, to insure tha meniscus 80 will wet a test element 71, FIG. 2, when it reaches that element. Second, it is configured to insure that the transported liquid completely wets surfaces 56 and 58 at the vicinity of aperture 70, as described in greater detail hereinafter.

Aperture 70 is characterized as a simple aperture that is, one having only a single flow portion. As used herein, "flow portions" are those parts of the aperture shape that are fee of substantial interior corners. Such portions are graphically determinable by sectioning the aperture shape along hypothetical lines connecting the substantial interior corners, if any. An interior corner, in turn, is a marked protruding demarcation in the wall curvature (as seen from inside the aperture) that cannot properly be considered to be an extension of the curvature prior to that demarcation. Mathematically, such corners are locations at which the first derivative of the surface changes abruptly in value. For a simple aperture, the entire cross-sectional flow-through area is the "flow portion". In contrast, a compound aperture has more than one flow portion. Examples are described hereinafter.

Figure 3:
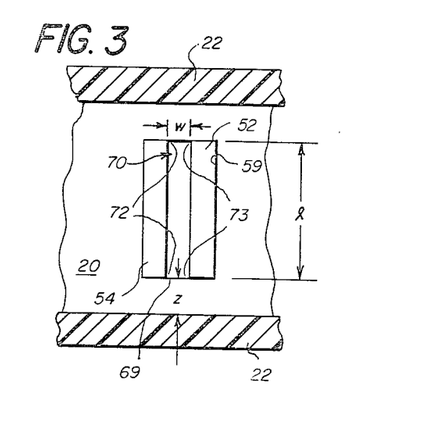
FIG. 3 is a fragmentary section view taken generally along the line III—III of FIG. 2.

In accordance with another aspect of the invention, the configuration of aperture 70 provides a length "l", FIG. 3, measured in a plane transverse to the direction of flow through the aperture along arrow 60, that exceeds the width "w" (or s$_2$) of the aperture. Most preferably, the ratio l/w is between about 2.5 and about 10.0.

Figure 5A:
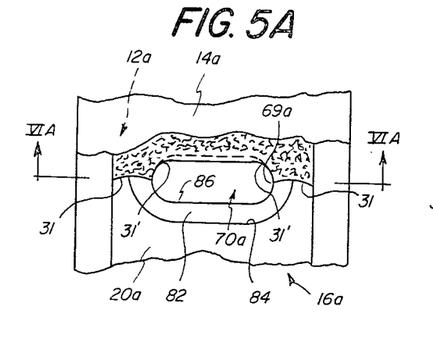
FIGS. 5A-5C are enlarged fragmentary plan views of an embodiment similar to that of FIG. 1, with a portion of top member 14a being broken away to illustrate the liquid flow pattern in the device into the aperture of the second zone.
Figure 5B:
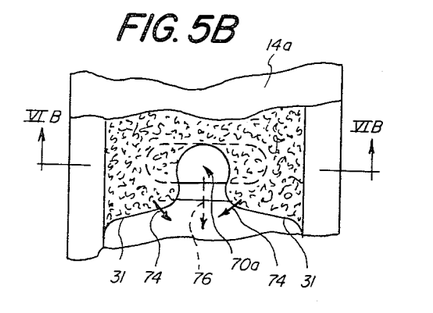
Figure 5C:
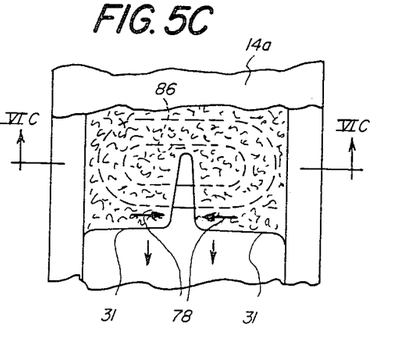

The corners 72 and 73 of aperture 70 are squared, FIG. 3, or they can be rounded as shown in FIGS. 5A-5C. Rounded corners are generally preferred. In the embodiment of FIG. 3, dimension "l" extends generally perpendicularly to the flow direction designated by arrow 32. Alternatively, aperture 70 can be rotated 90 degrees such that "l" is parallel to arrow 32. In such an arrangement, rounded corners are particularly preferred.

The thickness of member 16 defining the aperture, that is, the dimension "t", FIG. 2, is not believed to be a significant factor in determining the relationship of "l" and "w".

As is indicated in FIG. 1, a number of additional transport zones are extended from the single first zone 12, all downstream from access aperture 30 at predetermined locations. These additional zones each have a diverting aperture 70', 70'', and 70''', respectively, configured as described for aperture 70.

The dimeension for s$_1$ and s$_2$ are selected to maintain capillary flow of the liquid. Actual values will depend of course on the liquid being transported and the materials from which members 14 and 16 and 52 and 54 are selected. Preferred values for use with blood serum are 250 microns or less.

Optionally, an additional pair of opposing surfaces can be added to zone 50, in the form of opposing sidewalls 87, shown in phantom, FIG. 4. In such an embodiment, meniscus 80 wets all boundary surfaces and one or more vent apertures are provided in walls 52, 54 or 87.

The opposing surfaces of the second zone can be surfaces of one and the same member shaped as a tube, FIGS. 5A-5C and 6A-6C. Parts similar to those previously described bear the same reference numeral to which the distinguishing suffix "a" is appended. Thus, first capillary zone 12a is formed by opposing surfaces of members 14a and 16a, and sidewalls 22a. Aperture 70a is formed in surface 20a of member 16a, FIG. 5A, to divert liquid flow into the second zone 50a, FIG. 6A, in the manner described for the previous embodiment. However, aperture 70a is the aperture of a tubular member 82 inserted into an aperture 84 in member 16a. The surface 86 of tube 82 defines the opposing surfaces of zone 50a. As in the previous embodiment, the ratio l/w, FIG. 5A, is between about 2.5 and about 10.0.

The mechanism that permits the diverting aperture of the invention to operate to direct a portion of the flow into the second zone is not completely understood, nor is it necessary to the practice of the invention. However, the following description of the flow patterns for the embodiment of FIGS. 5A-5C and 6A-6C is believed to roughly illustrate the mechanism involved. Member 14a has been broken away for this purpose, FIGS. 5A-5C, leaving the liquid in position as it would be if the member 14a were fully in place.

Figure 6A:
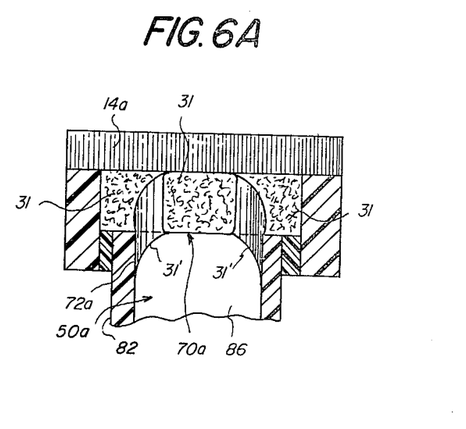
FIGS. 6A-6C are fragmentary section views taken generally along the line VIA—VIA through VIC—VIC of FIGS. 5A-5C.
Figure 6B:
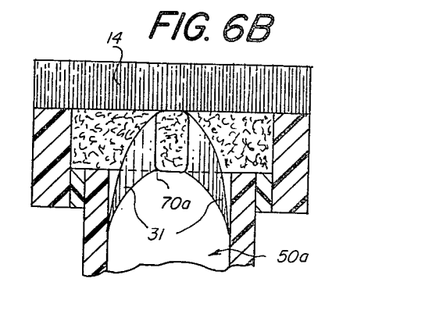
Figure 6C:
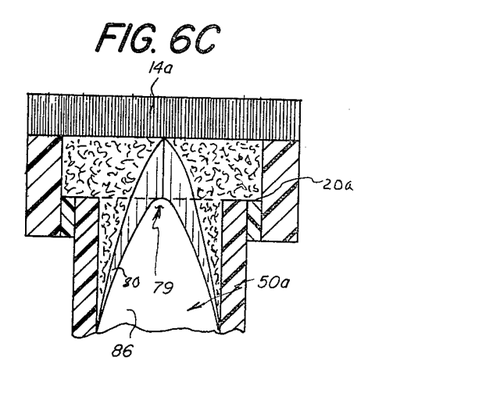

It is believed that the described configuration permits coalescence of the liquid within the aperture as illustrated in FIGS. 5A through 5C (and 6A through 6C). As meniscus 31, FIG. 5A, reaches aperture 70a, it moves past the sides 69a thereof as though to bypass it. However, a portion 31' of the meniscus moves into the aperture at corners 72a, FIG. 6A. As meniscus 31 continues to advance, FIGS. 5B and 6B, it tries to close upon itself in the direction of arrows 74. However, because of the shape selected for aperture 70a, the liquid coalesces and starts to fill aperture 70a and zone 50a. Air is pushed out of aperture 70a in the direction of arrow 76. Finally, before meniscus 31 completely closes on itself, arrows 78, FIG. 5C, aperture 70a fills up and all of surface 86 of member 82 located immediately below the surface 20 of the first zone, e.g., at the level of point 78, FIG. 6C, is completely wetted. It will be appreciated that the advancing portion of the new meniscus 80, FIG. 6C, has already wrapped itself around most of surface 86 at the point in time depicted, so that when closure of arrows 78 occurs, coalescence of the liquid in aperture 80 in zone 50a below surface 20a is complete. Point 79 becomes a line of intersection between the meniscus and surface 86, below first zone surface 20a. A new meniscus 80 has thus formed in zone 50a, and continues to advance through that zone.

If aperture 70a were as wide as it is long, e.g., if it were circular, then meniscus 31, FIG. 5B, would tend to close on itself before coalescence occurred and before the liquid filled aperture 70a and completely wetted surfaces 86. That is, coalescence would not occur at point 79 before the closure of the meniscus 31. The result would be a halt of the new meniscus at the aperture and zone 50a would not be filled.

Figure 7:
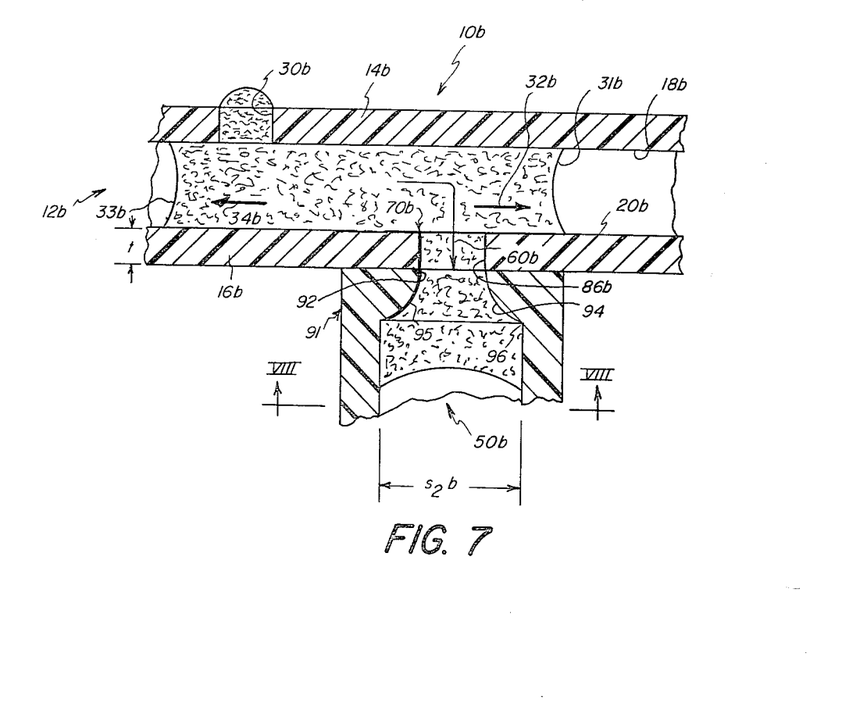
FIG. 7 is a section view similar to that of FIG. 2, but illustrating another embodiment.
Figure 8:
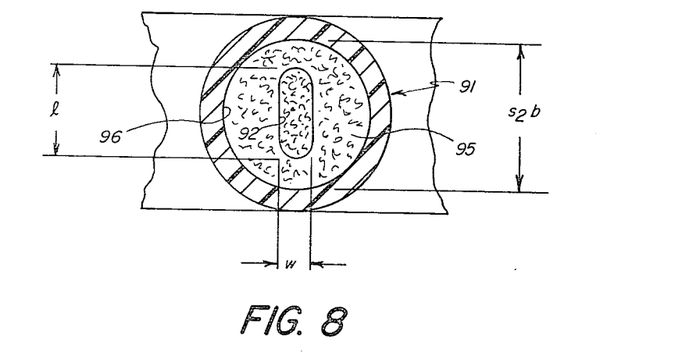
FIG. 8 is a fragmentary section view taken along the line VIII—VIII of FIG. 7.

An advantage in having opposing members of the second zone extend through to the first zone, FIGS. 2 and 6A-6C, is that such members can have surfaces with different contact angles compared to the opposing surfaces of the first zone, as an aid to flow within the zone. However, it is not critical to the invention that the opposing surfaces of the second zone extend all the way through the one member of the first zone to which they are attached. Furthermore, spacing between the opposing surfaces of the second zone need not be maintained constant, but can be increased or decreased. Both of these features are illustrated in the embodiment of FIGS. 7 and 8. Parts similar to those previously described bear the same reference numeral to which the distinguishing suffix "b" is appended. Thus, FIG. 7, device 10b comprises zone 12b formed by opposing surfaces 18b and 20b of members 14b and 16b, and aperture 30b permits introduction of liquid. Menisci 31b and 33b form and flow in directions 32b and 34b as in the previous embodiments. However, diverting aperture 70b that leads to zone 50b is the aperture in member 16b, shaped substantially the same as aperture 70a, FIG. 5A, with opposing surfaces 86b. Surfaces 86b of zone 50b are continued by the interior surfaces of a hollow member 91 that is mounted or adhered underneath member 16b. Member 19 features an aperture 92 formed by interior surface 95, that is identical in shape and size to aperture 70b. Interiorly of member 91, surface 95 expands and converts into a cylindrical surface, FIG. 8, having a spacing $s_2b$ between surface 95 that is greater than either width w or length l of apertures 92 and 70b. Capillary spacing is maintained for $s_2b$.

An important feature of surface 95 is that the widening of $5_2b$ occurs gradually, leaving no exterior corners at locations 94, FIG. 7, such as would comprise energy barriers to the flow of meniscus 80b. On the other hand, interior corners such as might occur at surface intersection 96 do not create such barriers.

It will be appreciated that curved portion 94 by which spacing $s_2b$ is gradually widened, can extend for any desired portion of the length of zone 50b.

As is apparent, a portion of the liquid flows via arrow 60b through diverting aperture 70b into zone 50b.

Figure 9A:
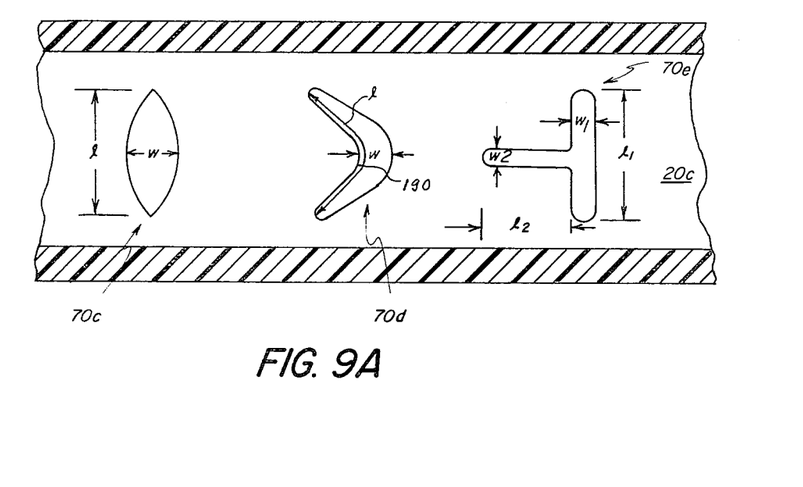
FIG. 9A is a fragmentary section view similar to that of FIG. 3, but illustrating additional embodiments.

A variety of shapes are useful for the diverting aperture, FIG. 9A. Parts similar to those previously described bear the same reference numeral to which the distinguishing suffix "c", "d", and "e" are appended. Thus, surface 20c features a diverting aperture 70c that has the shape of two concave surfaces of constant radii of curvature intersecting at two relatively sharp apexes, as shown in FIG. 9A. The ratio of "l" "w" is in the range noted above. This is currently the most preferred shape of the diverting aperture because this shape can tolerate greater values of w than can apertures such as aperture 70. Specifically, whereas aperture 70c can have a width up to about 3.0 mm, width w of aperture 70 is preferably less than that, e.g., no greater than about 1 mm. Tubular walls, not shown, extend below surface 20c as an extension of the zone initiated by aperture 70c.

The above-described diverting apertures have cross-sectional shapes that provide only concave surfaces, to the extent they are curved at all. Diverting aperture 70d is an example of a useful aperture with a convex surface 190. In such a shape, l is more properly measured as a total length of the cross-sectional flow-through area. The aperture is considered to be a simple aperture as the first derivative of surface 190 does not change abruptly.

The diverting aperture can be a compound aperture, aperture 70e, with more than one flow portion. In such a case, each flow portion must be examined to determine if, first, its cross-sectional flow-through area is 0.2 mm² *or less*. If it is, then flow in that flow portion can be expected to occur, regardless of the ratio of length to width for that portion. If however the flow-through area is greater than 0.2 mm², then the length and width of that portion are designed to provide a ratio l/w that conforms to the range noted above.

Figure 9B:
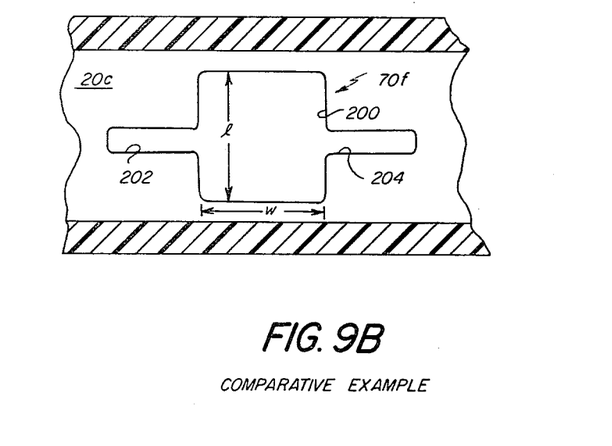
FIG. 9B is a view similar to that of FIG. 9A, but of a comparative example.

The apertures of FIG. 9A demonstrate that, given a total flow-through area greater than 0.2 mm², the shapes that work best are those that approximate aperture 70 of FIGS. 1 and 2, that is, are relatively long and thin when measured transverse to flow. Conversely, those apertures that tend not to work are those that approximate the shape of a square or circle. For example, a regular five-pointed star is unsatisfactory as it approximates more the shape of a square than it does a rectangle having a length at least 2.5 times the width. The aperture 70f of FIG. 9B is an additional example of an aperture that is inoperative for purposes of diverting liquid flow into the second zone. Such aperture has flow portions 200, 202 and 204, as determined by section lines (not shown) that can be drawn to connect the interior corners. Assuming that flow portion 200 has a cross-sectional flow-through area in excess of 0.2 mm², the ratio l/w for aperture 200 does not conform to the range of from about 2.5 to about 10.0. Instead l/w is about equal to unity. The presence of elongated portions 202 and 204 extending from portion 200 does not correct the deficiency, even though if used by themselves, portions 202 or 204 would be operative. The effect of such aperture 70f is to obtain initial flow partway into portions 202 and 204, but not portion 200. For that reason, the liquid does not completely wet the surfaces of the second zone downstream from aperture 70f, and does not continue to flow within the second zone.

On the other hand, if portion 200 were designed to have a cross-sectional flow-through area no greater than 0.2 mm², then aperture 70f would be operative.

Once the liquid flows into any of the transport zones, a variety of functions are performable on the liquid at different locations within the zone or zones. For example, test elements of various kinds can be disposed at test loci in the zones for contact with the liquid. FIGS. 10-13 illustrate a highly preferred form of such test elements, comprising ion-selective electrodes 114, hereinafter "ISE's", for evaluating the activity, and therefore, the concentration, of any electrolytes in the liquid. Parts similar to those previously described bear the same reference numeral to which the distinguishing suffix "g" has been attached.

Figure 13:
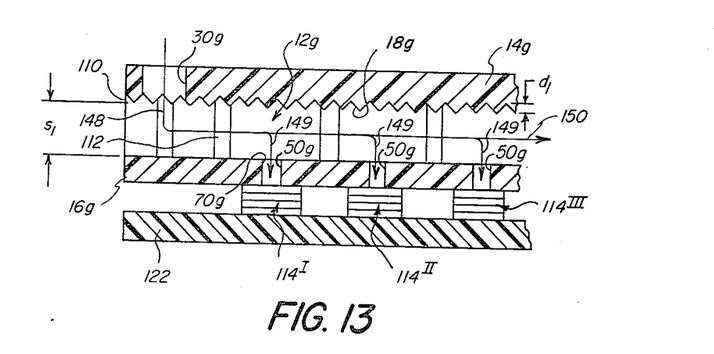

Thus, device 10g comprises a first transport zone 12g, FIG. 13, that is an ion bridge extending between and connecting matched pairs of ISE's $114^I$, $114^{II}$, $114^{III}$, and $114^{IV}$. Each of the ISE's is disposed in a second, third, fourth and fifth transport zone extending separately from zone 12g, as described hereinafter.

Figure 10:
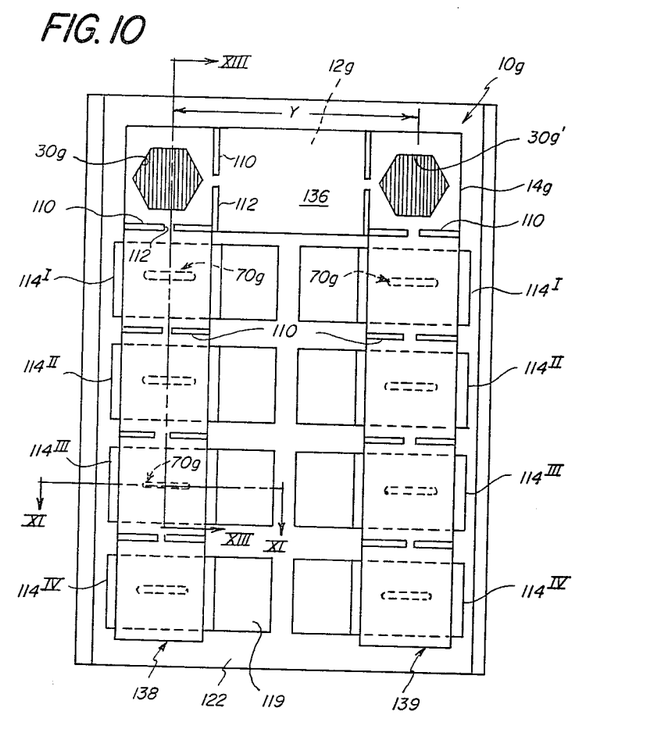
FIG. 10 is a plan view of yet another embodiment of the invention.
Figure 11:
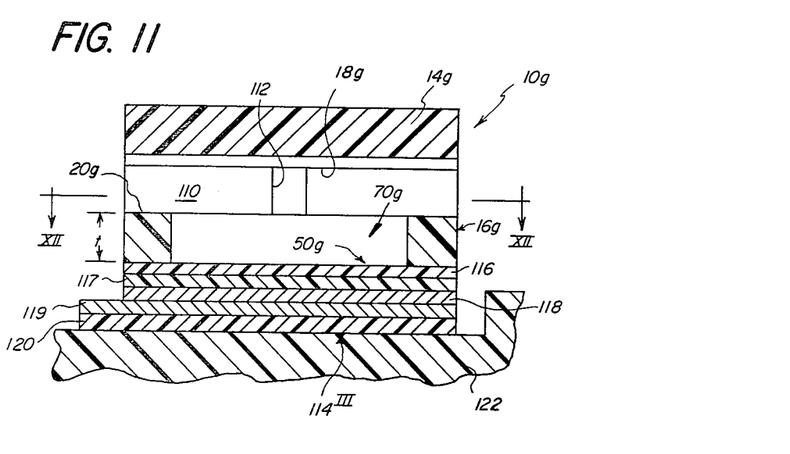
FIG. 11 is a fragmentary section view taken generally along the line XI—XI of FIG. 10.

More specifically, each of the ISE pairs is mounted, as by adhesive, on a frame 122, FIG. 10, and the pairs are connected by the ion bridge formed by the transport device 10g which comprises members 14g and 16g having opposed surfaces 18g and 20g, FIG. 11, as described for the previous embodiments. Preferably, at least surface 20g is provided with parallel grooves, FIGS. 11 and 13. A pair of liquid access apertures 30g and 30g' are formed in member 14g, preferably shaped as a hexagon, as shown in FIG. 10. To retard flow of liquid after it is introduced into the access apertures, gating walls 110 are formed within zone 12g, each with a gating aperture 112, described and claimed in my U.S. Application Ser. No. 101,662, filed Dec. 10, 1979, entitled "Liquid Transport Device Containing Means for Delaying Capillary Flow".

In accordance with another aspect of the invention, the paired ISE's are disposed in second, third, fourth, and fifth transport zones 50g extending from surface apertures 70g, FIGS. 11 and 13. In this embodiment, these zones extend only the thickness "t" of member 16g, FIG. 11, because the ISE's are adhered to the undersurface of member 16g with apertures 70g between them and first zone 12g. Thus the opposing surfaces of zone 50b are the opposing surfaces 86g of aperture 70g.

Figure 12:
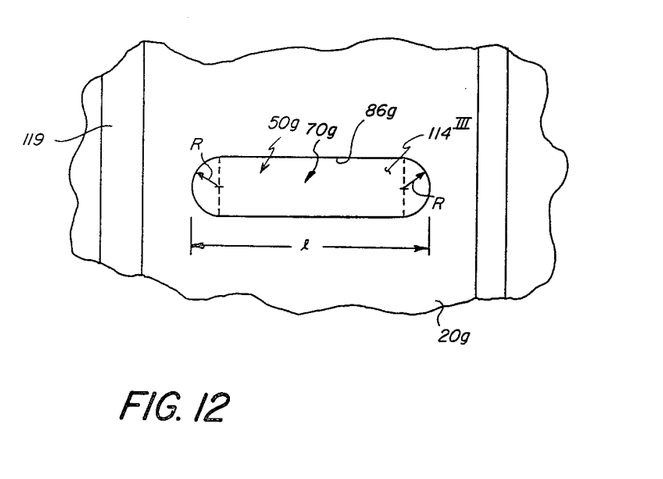
FIGS. 12 and 13 are section views taken generally along the line XII—XII and XIII—XIII respectively, of FIGS. 11 and 10.

As with the previous embodiments, aperture 70g has a length l, FIG. 12, that is greater than the width w, here equal to twice the radius R. Most preferably, the same ratio range described above applies to the ratio of l and 2R.

As described in U.S. Pat. No. 4,053,381, issued on Oct. 11, 1977, the details of which are expressly incorporated herein by reference, each ISE 114 is a generally flat multilayered element comprising three or more adjacent layers 116–120, FIG. 11. A quantity of whole blood or serum makes contact with, e.g., a layer 116, after having traversed zones 12g and 50g from one of the apertures, e.g., aperture 30g. Layer 116 is an ion-selective membrane containing an ionophore and a solvent, so that the ion $Z \oplus$ of choice is carried or otherwise effectively penetrates to the underlying layers 117 and 118 where an electrical potential is generated proportional to the activity of that particular ion. Layer 117, in one embodiment, is a dried hydrophilic binder containing the salt $Z^{\oplus}X^{\ominus}$. Layer 118 in such instances is the $X^{\ominus}$ salt of an electrically conductive metal $M^{\oplus}$, and metal $M°$ forms layer 119. Because layer 119 is an electrically conductive layer, a potential is measurable by an electrometer, not shown, via probes which contact layer 119. Because the ISE's are paired, the other member of the pair is contacted with a reference liquid having a known activity of the electrolyte in question. Such reference liquid is transported simultaneously from the other aperture, e.g., aperture 30g', through zones 12g and 50g. The reference liquid and blood or blood serum flow together at portion 136 of zone 12g, FIG. 10, to form a junction, permitting the electrical readings to be made. Any difference in the potentials measured at the paired electrodes is due to the two different ion activities of the two liquids. The difference is registered as a difference potential on the electrometer and converted into a measure of concentration of the ionic analyte $Z \oplus$ as is conventional.

If the ISE pair is to measure $Cl^{\ominus}$, layers 116 and 117 are preferably replaced by an interferant-barrier overcoat layer. Such a layer comprises, e.g., cellulose acetate containing a polyol.

It will be appreciated that each of the electrode pairs 114 is specific to the analysis of a different one of the analytes. For the differential mode of measurement, each ISE of any pair is identical to the other of the pair. Thus, the two electrodes for one electrode pair $114^I$ is constructed and adapted to detect $K^{\oplus}$, the two electrodes for pair $114^{II}$ to detect $Na^{\oplus}$, the two electrodes for pair $114^{III}$ to detect $Cl^{\ominus}$, and the two electrodes for pair $114^{IV}$ to detect $HCO_3^{\ominus}$. The chemistries of the layers of the electrodes are not part of this invention, and comprise generally that described above for ion $Z \oplus$ with the appropriate selection of an ionophore for layer 116. For example, in the case of the $K^{\oplus}$ electrodes, layer 116 contains an ionophore such as valinomycin or one of the others listed in *Research Disclosure,* Vol. 161, Publication No. 16113, Sept. 1977, 2nd col. of p. 32, published by Industrial Opportunities Limited, Homewell, Havant Hampshire PO91EF, United Kingdom, the contents of which are expressly incorporated herein by reference. For the $Na^{\oplus}$ electrodes, the ionophore is preferably methyl monensin, and for $HCO_3^{\ominus}$ the ionophore is preferably 4-octyl trifluoroacetophenone and the solvent is trioctyl propylammonium chloride. For the $Cl^{\ominus}$ electrodes, layers 116 and 117 are replaced as described earlier.

In use, a quantity of sample to be tested is deposited, preferably as a drop, in one of apertures 30g and 30g' and a quantity of reference liquid in the other. The liquids spread by capillary action in a flow pattern that is partially shown by arrows 148 and 149, FIG. 13.

That is, the liquid introduced at the locus provided by aperture 30g, flows through zone 12g, and a portion then flows into each of the apertures 70g and into zones 50g while the remainder continues to flow within zone 12g, arrow 150. The liquid also flows into portion 136, FIG. 10, to contact the reference liquid deposited at 30g'. The reference liquid also contacts its ISE's positioned adjacent to the opposite branch of the ion bridge.

To vent air trapped, at least portions of the edges 138 and 139, FIG. 10, of members 14b and 16b are left open to the atmosphere. No additional vent means, such as apertures, are necessary for zones 50g due to the short distance t, FIG. 11, traversed in zone 50g. However, such apertures are preferred if the length of zones 50g is extended. Dimension t is preferably no larger than about 100 microns if no vent apertures are present.

In the transport of the blood serum, such as in the use described in the embodiment of FIGS. 10–13, it is preferred that the dimensions of the device of the invention be chosen as follows. For a grooved plastic surface 20g having a groove depth $d_1$ of between about 3 and about 14 microns, FIG. 13, the effective spacing $s_1$ between the two surfaces can be varied between about 0.05 mm and about 0.5 mm for best results. Highly preferred values are between about 0.125 mm and about 0.25 mm. Lesser values of $S_1$ are useful, except that when the separation distance $S_1$ approaches zero, spreading through the zone becomes extremely delayed.

If grooves are used at all, a preferred range for the width of the grooves is between about 5 microns and about 5 mm, it being noted that beyond about 5 mm, the rate and direction of spreading becomes insignificantly different from the results achieved by a nominally smooth surface.

A representative example within the aforedescribed ranges of $d_1$ $s_1$, l and R for the above-described potentiometric analysis of blood serum is as follows:

EXAMPLE $s_1 = 100$ microns
$d_1 = 6.8$ microns
$l = 2.0$ mm
$R = 0.2$ mm
$t = 75$ microns
Distance y between apertures 30g and 30g', FIG. 10, = 10 mm.

Preferred materials for at least the opposing surfaces of the members of either the first or second zone are non-fibrous materials that are substantially impervious to blood serum. Examples of such materials include acetates such as cellulose triacetate, cellulose acetate propionate, and cellulose acetate butyrate; polystyrene; polyethylene; polypropylene; ABS plastic; and polycarbonate. Such surface materials permit various chemical coatings to be applied, if desired, for example, surfactants.

It will be appreciated that a significant advantage of the construction of the ion bridge as described above is its generally open configuration in an enclosed environment that nevertheless provides a controlled flow. Such a configuration leaves ample room for the flow of whole blood, unlike ion bridges which utilize porous absorbent means with void volumes less than about 50%. Furthermore, the materials described in the preceding paragraph, by being free of fibers, avoid the possibility of shorting out the ISE's.

Because the total environment is generally a closed one, evaporation from, and contamination of, zone 12g are minimized. Dissolved gases tend to be retained in the liquid transported, particularly when the lateral distance x, FIG. 2, between the access aperture and the second transport zones, is at least 1 cm. Such prevention of gas loss is particularly important if a dissolved gas is being tested, for example, $HCO_3{}^{\ominus}$ tested using ISE's 114 of FIG. 10.

The invention has been described in detail with particular reference to preferred embodiments thereof, but it will be understood that variations and modifications can be effected within the spirit and scope of the invention.

What is claimed is:

1. In a liquid transport device comprising
   (a) a first pair of opposing surfaces spaced apart a distance effective to induce capillary flow of introduced liquid and to create a first zone of intended capillary liquid transport between said surfaces, and
   (b) liquid access means permitting introduction of liquid into said first zone, whereby introduced liquid flows downstream from said access means by capillary attraction;
   the improvement comprising at least a second pair of opposing surfaces spaced apart a distance effective to induce capillary flow of introduced liquid and to provide a second zone of intended capillary liquid transport, said second pair of surfaces extending from only one of said first pair of surfaces, and diverting means in said one surface for directing a portion of the liquid away from said first zone into said second zone while the remainder of the liquid continues flowing in said first zone, said diverting means being
   (i) located downstream from said access means at a predetermined location and
   (ii) configured to insure complete wetting of said second pair of surfaces downstream from said one surface by the liquid moving therepast, and to provide a cross-sectional flow-through area greater than about 0.2 mm$^2$.

2. A device as defined in claim 1, wherein said diverting means comprises an aperture in said one surface containing one or more flow portions, each of said portions either
   (a) having a length and a width, measured in a plane transverse to the direction of liquid flow through said flow portion, such that the ratio of the length to the width is between about 2.5 and about 10.0, or
   (b) having a cross-sectional flow-through area no greater than about 0.2 mm$^2$;
   whereby liquid will completely fill said aperture to maintain capillary flow therethrough while liquid flow continues in said first zone.

3. A device as defined in claim 1, and further including a test element in said second zone.

4. A device as defined in claim 1, and further including a test element disposed adjacent said diverting means with said diverting means between said first zone and said element.

5. A device as defined in claim 3 or 4, wherein said test element is an ion-selective electrode.

6. A device as defined in claim 1, wherein the direction of flow through said diverting means extends generally perpendicularly to the primary flow direction within said first zone.

7. A multidirectional capillary liquid transport device, comprising first and second zones of connected but separately extending capillary transport, each of said zones comprising at least two opposing surfaces spaced apart a distance effective to induce capillary flow of introduced liquid in that zone;
   access means to permit introduction of the liquid into said first zone, whereby liquid flows into said first zone donwstream from said access means by capillary attraction; and
   vent means in at least said first zone for venting trapped air from said first zone;
   the surfaces of said second zone extending from only one surface of said first zone at an aperture in said one surface, said aperture being disposed downsteam from said access means at a predetermined location and containing one or more flow portions each of which either
   (a) has a length and a width measured in a plane transverse to the direction of liquid flow through said flow portion such that the ratio of the length to the width is between about 2.5 and about 10.0, or
   (b) has a cross-sectional flow-through area no greater than about 0.2 mm$^2$;
   the total cross-sectional flow-through area of said aperture being greater than about 0.2 mm$^2$.
   whereby flowing liquid encountering said aperture completely flows into said second zone to maintain capillary flow therethrough while liquid flow continues in said first zone.

8. A device as defined in claim 7, wherein the direction of flow through said aperture extends generally perpendicularly to the primary flow direction within said first zone.

9. A device as defined in claim 7, and further including a test element in said second zone.

10. A device as defined in claim 9, wherein said test element is an ion-selective electrode.

* * * * *

UNITED STATES PATENT AND TRADEMARK OFFICE
CERTIFICATE OF CORRECTION

PATENT NO. : 4,271,119
DATED : June 2, 1981
INVENTOR(S) : Richard L. Columbus

It is certified that error appears in the above-identified patent and that said Letters Patent are hereby corrected as shown below:

Col. 1, line 48, "through", should read --though--.

Col. 4, line 62, "grooves", should read --grooved--.

Col. 5, line 52, "dimeension", should read --dimensions--.

Col. 6, line 36, "78", should read --79--.

Col. 7, line 20, "5$_2$b", should read --S$_2$b--; line 37, after "1", insert --to--.

Col. 9, line 13, after "e.g.,", delete --a--; line 41, after '⊕', insert --,--.

Col. 10, line 33, "S$_1$", should read --s$_1$--; line 34, "S$_1$", should read --s$_1$--.

Signed and Sealed this

Seventeenth Day of July 1984

[SEAL]

Attest:

GERALD J. MOSSINGHOFF

Attesting Officer        Commissioner of Patents and Trademarks